United States Patent [19]

Rosenbaum et al.

[11] 4,123,498
[45] Oct. 31, 1978

[54] PROCESS FOR SEPARATING FISSION PRODUCT MOLYBDENUM FROM AN IRRADIATED TARGET MATERIAL

[75] Inventors: Herman S. Rosenbaum, Fremont; Douglas R. Packard, Sunol; Harry A. Levin, Livermore, all of Calif.

[73] Assignee: General Electric Company, San Jose, Calif.

[21] Appl. No.: 769,576

[22] Filed: Feb. 17, 1977

[51] Int. Cl.$^2$ ............................................. C01G 39/00
[52] U.S. Cl. ............................................. 423/2; 423/59
[58] Field of Search ............................ 423/2, 59, 606; 252/301.1 R; 424/1

[56] References Cited

U.S. PATENT DOCUMENTS

| | | | |
|---|---|---|---|
| 1,629,004 | 5/1927 | Schwarzkopf | 423/606 |
| 1,815,132 | 7/1931 | Schwarzkopf | 423/606 |
| 3,833,469 | 9/1974 | Robson | 252/301.1 R |
| 3,848,050 | 11/1974 | Jemal | 423/606 |
| 4,017,583 | 4/1977 | Motojima et al. | 423/2 |

OTHER PUBLICATIONS

Motojima II, *International Journal of Applied Radiation and Isotopes*, 27, 495–498, Pergamon Press (1976), Northern Ireland.

Castleman et al., *Nuclear Science and Engineering*, 29, 159–164, (1967).

*Primary Examiner*—Edward A. Miller
*Attorney, Agent, or Firm*—Ivor J. James, Jr.; Sam E. Laub; Samuel E. Turner

[57] ABSTRACT

A process for the separation and collection of molybdenum-99 from an irradiated uranium-containing target material utilizes thermal chromatographic separation. The irradiated target material containing the molybdenum-99 is heated in an oxidizing atmosphere to form an oxidized target material and gaseous molybdenum-99 trioxide. The gaseous molybdenum-99 trioxide is carried by the oxidizing atmosphere along with other vaporized materials to a cooling zone for progressive condensation and collection of the molybdenum-99 trioxide and the other materials in the form of separate deposits.

12 Claims, 2 Drawing Figures

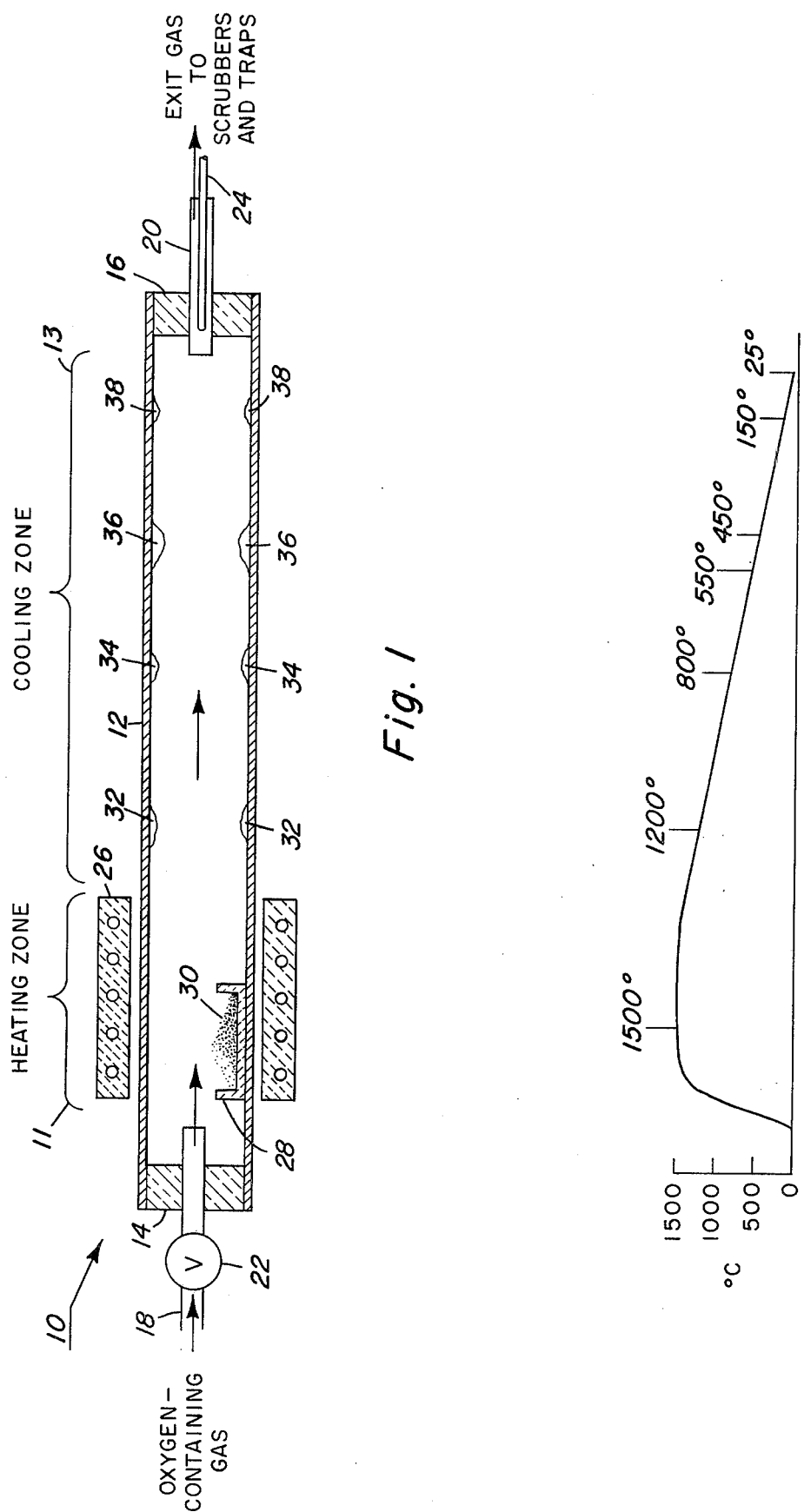

PROCESS FOR SEPARATING FISSION PRODUCT MOLYBDENUM FROM AN IRRADIATED TARGET MATERIAL

BACKGROUND OF THE INVENTION

This invention relates to a process for extracting and separating fission product molybdenum from an irradiated uranium-containing target material.

Technetium-99m is an extremely useful tool for medical applications and diagnosis. This radioisotope is used in a variety of applications in medical diagnosis. It is well suited for brain, thyroid, liver, lung blood pool and tumor scanning. It is preferred over the other radioisotopes because of the selective uptake by specific organs, its short half-life and low radiation dose rate which reduces the exposure of the patient to radiation. In addition, technetium-99m can also be used in industrial applications, such as measurement of flow rates, process control and the like.

Since the radioisotope technetium-99m has a short half-life (6 hours), it is common practice to use a molybdenum-99-technetium-99m generator to provide a supply of the technetium-99m. Basically, such a generator is made by sorbing the molybdenum-99 parent radioisotope, which has a 66-hour half-life, on an anion exchange material such as alumina. Subsequent decay of the molybdenum-99 produces the technetium-99m which can be selectively separated as needed from the generator by elution with a saline solution (which yields the technetium-99m as sodium pertechnetate).

Conventionally, technetium generators have been charged with molybdenum-99 which has been obtained by neutron bombardment of natural molybdenum or enriched molybdenum-98. A minor proportion of the molybdenum-98 is converted to its radioisotope molybdenum-99 by neutron capture. Radioactive molybdenum so prepared is referred to as "neutron product molybdenum".

Molybdenum-99 can also be obtained as a fission product from neutron bombardment of uranium-235. This "fission product molybdenum" is available in the form of sodium molybdate or ammonium molybdate solutions having a much higher specific activity than the maximum attainable from neutron product molybdenum. By using the more highly active fission product molybdenum for loading a technetium generator, a generator can be prepared which yields sodium pertechnetate eluates of exceptionally high radioactivity and which are consequently very desirable for certain medical applications.

The production of fission product molybdenum usually is done using a target comprising a mixture of aluminum and uranium, generally about 75 percent aluminum by weight with the balance being uranium highly enriched with uranium-235. This production requires an extraction process for extracting the molybdenum-99 from the target. The process currently used for extracting fission product molybdenum (molybdenum-99) from an irradiated aluminum-uranium target involves dissolving it in a strongly alkaline aqueous solution, such as sodium hydroxide. The resulting solution is filtered to separate the uranium and insoluble fission products from the molybdenum-bearing alkaline solution. The solution is acidified with sulfuric acid, and molybdenum-99 is separated from the solution by extraction with bis (2-ethyl-hexyl) phosphoric acid. This yields a molybdenum-99 containing extract from which residual soluble fission products are removed by stripping with organic solvents. This process is effective in extracting the molybdenum-99 from the irradiated target, but it produces a large volume of highly radioactive liquid waste. For example, approximately 33 liters of liquid waste is generated in the production of 4000 Ci of molybdenum-99. This presents a costly liquid waste disposal problem necessitating the use of difficult handling procedures. Accordingly, it is desirable to provide a process for extracting the molybdenum-99 from the target material and simultaneously separating the molybdenum-99 from the other fission products in a manner avoiding the creation of large volumes of liquid wastes.

Various processes have been devised for the separation of fission products from an irradiated target material. In Nuclear Science and Engineering, Volume 29, Number 2, August, 1967, at pages 159–164, A. W. Castleman, Jr. and I. N. Tang describe the results of an experimental study of the behavior of fission products released into helium and air from target materials of metallic uranium and a uranium-3.5% molybdenum alloy. This experiment used a thermochromatographic technique for investigating the nature of low-concentration gas species and this was applied to the release from these target materials of fission products barium, lanthanum, cerium, and molybdenum. Barium, lanthanum, and cerium were found not to be released into air in significant quantities because of the low volatility of their respective oxides, but molybdenum was released as $MoO_3$ in air. The same authors also report the chemical nature of fission products iodine and cesium vaporized from irradiated specimens into helium and air in the Journal of Inorganic & Nuclear Chemistry, Volume 32, Number 4, April, 1970, at pages 1057–1064. The same approach was used by E. A. Aitken et al for an investigation described in an article in the Transactions of the American Nuclear Society, Volume 14, Number 1, pages 176–177. In this article, the reactions of fission products in urania-plutonia fuels held in stainless steel fuel cladding were investigated.

Kenji Motojima et al disclose a method of separating molybdenum-99 from irradiated uranium dioxide by sublimation in the International Journal of Applied Radiation and Isotopes, Volume 27, pages 495–498 (1976). The irradiated uranium dioxide is converted to $U_3O_8$ by heating at about 500° C. in an oxygen atmosphere and then the nuclides (Mo-99, Te-132, and Ru-103) are separated from the $U_3O_8$ by heating at 1200° C. under vacuum.

However it remains desirable to provide a process in which the separation of the molybdenum is conducted simultaneously with the oxidation of the target material.

SUMMARY OF THE INVENTION

This invention comprises a process for the separation and collection of molybdenum-99 from an irradiated enriched uranium-containing target material. The process is carried out in a thermochromatographic zone comprising a heating zone and a cooling zone. The irradiated target material is heated in the heating zone in the presence of a flowing oxidizing atmosphere at a temperature sufficient to oxidize the oxide forming constituents of the target material, drive off the fission product gases and sublime the sublimable materials either initially present in the target material or formed during the heating step. The flowing oxidizing atmosphere carries the vaporized and sublimed materials and passes from the heating zone through the cooling zone. The temperature in the cooling zone decreases from that of the heating zone to near room temperature so the temperature of the oxidizing atmosphere is controllably decreased as the atmosphere passes through the cooling zone. The sublimed and vaporized materials in the atmosphere are progressively condensed and collected at successive locations in the cooling zone (and thus separated from one another in the form of deposits) as the temperature of the atmosphere is decreased. The separated materials, including molybdenum-99 trioxide, are then recovered from the cooling zone.

OBJECTS OF THE INVENTION

It is an object of this invention to provide a process for separating molybdenum-99 from an irradiated target material without generating large volumes of radioactive liquid waste and encountering the cost of disposing of such waste.

Another object of this invention is to provide a process for separating molybdenum from an irradiated target material utilizing the oxidizing atmosphere for two functions, namely for oxidizing the irradiated target material and for transporting the gaseous products emanating from the oxidized target material to a lower temperature location for collection of sublimates from the gaseous products.

Still another object of this invention is to provide a process achieving very high recovery of molybdenum-99 from an irradiated target material in an efficient and economical manner.

Other objects and advantages will become apparent to the person skilled in the art from reading the following description of this invention and by reference to the attached drawings briefly described in the following paragraphs.

DESCRIPTION OF THE DRAWINGS

FIG. 1 is a sectional view of a thermochromatographic column used to practice the process of this invention on an irradiated target material in particulate form.

FIG. 2 is a graph showing the temperature in ° C. along the thermochromatographic column of FIG. 1.

DESCRIPTION OF THE INVENTION

Referring now to FIG. 1, an apparatus (thermochromatographic column) 10 is comprised of a nonreactive tube 12 (such as quartz or high purity alumina) having removable plugs 14 and 16 at its ends. Oxidizing gas inlet tube 18, provided with control valve 22, opens through plug 14 and gas exit tube 20 opens through plug 16. A source (not shown) of an oxidizing gas, such as oxygen or air, is connected to inlet tube 18. A movable quartz-clad closed-end tube 24 housing a thermocouple is positioned in exit tube 20 for use in measuring the temperature at different points along the length of tube 12.

A heating means 26 is provided at one end of the quartz tube, and a preferred heating means 26 is in the form of an electrical resistance heater. The heated end of tube 12 constitutes the heating zone 11. The remainder of tube 12 constitutes the cooling zone 13 that is cooled by heat lost to the surrounding atmosphere. The heat loss is such that a temperature profile for the tube 12 is developed as shown in FIG. 2 for a maximum temperature in the heating zone of about 1500° C.

The tube 12 and plugs 14 and 16 define a thermochromatographic zone when the heating means 26 is in operation.

During the practice of the process of this invention, an irradiated uranium-containing target material is introduced to the heating zone portion of the thermochromatographic zone. In FIG. 1 the container 28 is shown holding the target material 30 in particulate or powder form. Container 28 is typically made of a refractory material, such as platinum or alumina, suitable for use in elevated temperature furnaces. After insertion of the target material, a flow of an oxidizing gas successively through the heating zone and the cooling zone is started and heating means 26 is turned on. The irradiated target material is thus heated in the presence of an oxidizing atmosphere to a temperature sufficient to oxidize the oxide-forming components of the target material, drive off the fission product gases, and sublime the sublimable materials either initially present in the target material or formed during the heating step. A temperature of at least about 1000° C. is required and preferably a temperature in the range of about 1000° C. to about 1600° C. is used. One sublimable oxide formed is molybdenum-99 trioxide from the fission product molybdenum present in the target material. The flow of the oxidizing gas through the heating zone 11 carries the gaseous oxides and any gaseous fission products emitted from the irradiated target during heating into cooling zone 13.

In cooling zone 13, the gaseous products susceptible of forming sublimates do so according to their respective vapor pressures as the gas temperature decreases according to the temperature profile in FIG. 2. In this manner there is a thermochromatographic separation and collection of the sublimates in the form of deposits in different locations on the inner surface of tube 12. In greater detail the temperature gradient in the cooling zone 13 permits effective separation of the various sublimed materials to provide maximum localization of the sublimates in the form of separate deposits. Typical sublimates collected are illustrated in FIG. 1. Deposit 32 represents a small amount of $U_3O_8$, deposit 34 represents a deposit of $Cs_2O$, deposit 36 represents a deposit of $MoO_3$ and deposit 38 represents a deposit of iodine. Iodine is transported to the coolest part of the cooling zone since it, of those materials condensible, exhibits the highest vapor pressure. Molybdenum, the desired product in the form of $MoO_3$ will be deposited on the tube 12 at a specific location between the target material 30 and the plug 16. The gaseous fission products, such as xenon and krypton, do not condense at all at atmospheric temperature and pressure, and are carried in the gas stream exiting the apparatus 10 for collection.

The process of this invention is modified when the target material is in the form of pellets. In such a case, a two stage heating step is employed. The pellets are first heated to and maintained at a temperature sufficient to convert the pellets into a powder, i.e., a temperature in the range of about 400° to about 600° C. for a time in the range of about 1 to about 3 hours. The target material is reduced to a powder in order to facilitate substantially complete release of the molybdenum in the form of gaseous molybdenum trioxide. Then the temperature is raised to at least about 1000° C., preferably from about 1000° to about 1600° C. to achieve oxidation of the target material and sublimation of the sublimable materials.

The recovery of the molybdenum from tube 12 can be facilitated by making the portion of the tube 12 removable where the deposit of molybdenum trioxide occurs. Recovery of the MoO₃ from the tube 12 is conveniently accomplished by dissolving the molybdenum trioxide in a caustic solution or by mechanical removal such as brushing the deposit from tube 12.

It is possible to mix the oxidizing gas (e.g., air or pure oxygen) with a carrier gas. Typical carrier gases are non-reactive gases such as nitrogen and the inert gases, such as argon, helium and neon or other oxidizing gases such as carbon dioxide. In practice carrier gases comprising from 20 percent up to about 80 percent by volume can be used in a mixture with the oxidizing gas.

Typical gas flows for the oxygen-containing gas through the chromatographic zone in the process of this invention are in the range of 1 cubic foot/hour to 10 cubic feet/hour.

Several different compositions can be used for target material prior to irradiation. One preferred composition is uranium dioxide in which uranium-235 comprises about 93% by weight of the uranium in the uranium dioxide. Another composition is comprised of a comparably enriched pure uranium metal. The process of this invention has the advantage of being an anhydrous process. The process does not produce any significant amount of radioactive liquid wastes and has no liquid waste disposal problem.

The utilization of the oxidizing gas to transport the gaseous products from the oxidized target material in the heating zone into the cooling zone achieves more rapid and efficient separation and collection of the molybdenum-99 from the irradiated target material. The process of this invention offers an advantage of very high release rates for molybdenum from the target material and in practice releases rates of 99% by weight or more are achieved.

Those skilled in the art will gain a further understanding of this invention from the following illustrative, but not limiting, example of this invention in which the percentages are based on weight, unless otherwise stated.

EXAMPLE

Starting Material Preparation

About 50 grams of ceramic grade unenriched uranium dioxide powder of particle size less than 325 mesh were placed in a container. From a first portion of this powder, four cylindrical control pellets each weighing about 10 grams, ½ inch in diameter and ½ inch in height were pressed.

The remaining portion of uranium dioxide powder was divided into four generally equal lots to which various additions of natural molybdenum powder of particle size less than 325 mesh were added to produce four different UO₂ powder lots containing respectively, 50 parts per million (p.p.m.), 100 p.p.m., 300 p.p.m. and 700 p.p.m. natural molybdenum. Natural molybdenum is comprised of the following: 15.84% Mo-92, 9.04% Mo-94, 15.72% Mo-95, 16.53% Mo-96, 9.46% Mo-97, 23.78% Mo-98 and 9.63% Mo-100. The four resulting uranium dioxide-molybdenum mixtures were separately blended for uniformity in a Specs Industries blender, and 4 pellets from each lot weighing either 2 grams or 10 grams were pressed.

All the pellets prepared, both UO₂ control and UO₂-Mo mixture pellets, were sintered under an atmosphere of dry hydrogen (having less than 10 p.p.m. by volume H₂O) at 1750° C. for 4 hours. The molybdenum content of each pellet was determined by chemical analysis of the powder from which the pellet was pressed using the Dithiol method.

Molybdenum Release Test

A group of five pellets was selected from those prepared as described above, including one control pellet and one pellet each from the four different molybdenum-containing lots. This group was given the arbitrary description of pellet lot A.

Each pellet was crushed to a powder and the powders were placed in separate platinum crucibles and a small portion of the powder from each crucible was taken for chemical analysis. The crucibles containing the remainder of the powders were simultaneously treated according to the process of this invention in the same furnace. The process was carried out in an atmospherically controlled electrically heated tubular furnace manufactured by the Heraeus Company. The furnace had a high purity cylindrical alumina tube 30 inches in length, one inch in outer diameter and ¼ inch in wall thickness. The resistance heating element surrounded approximately 15 inches of the tube and was positioned in the middle of the tube leaving approximately 7½ inches of cooling zone cooled by loss of heat to the surrounding atmosphere.

The furnace containing all the crucibles was heated from room temperature at a rate of 7° C. per minute to a maximum temperature of 1500° C. and held at that temperature for 18 hours. A gas atmosphere of pure oxygen was passed through the furnace at a rate of one cubic foot per hour, flowing first into and through the heating zone and then through the cooling zone.

Upon examination after completion of the heating, the oxidized powders were noted to have volatilized some of the uranium oxide. A deposit of what appears to be uranium oxide was found within the furnace tube downstream from the heating element at a point where the temperature was approximately 1200° C. The deposit was not analyzed but was believed to be U₃O₈. A yellow deposit determined by x-ray fluorence to be molybdenum trioxide was noted at another point further downstream in the cooling zone at a location indicative of 500° C. ± 50° C., and this deposit was easily removed from the tube. Table II gives the pellet identity by attempted molybdenum addition, the molybdenum content of the crushed pellets prior to oxidation, and the molybdenum content of the residual powder in the crucibles removed from the furnace.

TABLE I

| | LOT A | |
|---|---|---|
| Pellet Identity by Attempted Mo Addition (p.p.m.) | Mo Content Prior to Oxidation (p.p.m.) | Mo Content After Oxidation (p.p.m.) |
| 0 | 3.8 | 1.0 |
| 50 | 35.9 | 1.7 |
| 100 | 77.7 | 4.5 |
| 300 | 256.8 | 1.0 |
| 700 | 545.7 | 6.1 |

This demonstrates that release of more than 99% by weight of the molybdenum contained in a material can be achieved by the practice of the process of this invention.

It is to be understood that although the invention has been described with specific reference to particular embodiments thereof it is not to be so limited, since changes and alterations therein may be made which are within the full intent and scope of this invention as defined by the appended claims.

What is claimed is:

1. A process for the separation and collection of molybdenum-99 from an irradiated enriched uranium-containing target material, the process comprising the steps of
    (a) establishing a thermochromatographic zone having a heating zone and a cooling zone cooled by atmospheric cooling,
    (b) passing an oxidizing atmosphere successively through said heating and cooling zones,
    (c) heating the target material in the heating zone at a temperature less than the melting point of said target material, said temperature being sufficient to drive off fission product gases, oxidize oxide-forming components of the target material and subline sublimable materials including molybdenum-99 trioxide into said oxidizing atmosphere to form a gaseous mixture to be carried into said cooling zone, and
    (d) cooling the gaseous mixture in said cooling zone so that the sublimed materials including the molybdenum-99 trioxide are progressively condensed and collected at successive locations in the cooling zone in the form of substantially separate deposits.

2. A process according to claim 1 in which the uranium-containing material from which the irradiated target material is formed comprises metallic uranium in which the uranium is 93% by weight uranium-235.

3. A process according to claim 1 in which the uranium-containing material from which the irradiated target material is formed comprises metallic uranium in which the uranium is 93% by weight uranium-235.

4. A process according to claim 1 in which the heating zone is maintained at a temperature in the range of about 1000° to about 1600° C.

5. A process according to claim 1 in which the oxidizing atmosphere is comprised of oxygen.

6. A process according to claim 1 in which the oxidizing atmosphere is comprised of air.

7. A process according to claim 1 in which the oxidizing atmosphere is comprised of oxygen and a carrier gas.

8. A process according to claim 7 in which the carrier gas is comprised of nitrogen.

9. A process according to claim 7 in which the carrier gas is comprised of an inert gas.

10. A process according to claim 1 in which the irradiated target material is in powder form and the heating zone is maintained at a temperature in the range of about 1000° to about 1600° C.

11. A process according to claim 1 in which the irradiated target material is in pellet form and the heating is initially conducted at a temperature in the range of 400° to about 600° C. and maintained in this temperature range until the pellets are converted to a particulate form and then the heating is continued to a maximum temperature in the range of about 1000° to about 1600° C.

12. A process for the separation and collection of molybdenum-99 from an irradiated enriched uranium-containing target material, the process comprising the steps of:
    (a) passing an oxidizing atmoshpere successively through a heating zone and a connected cooling zone cooled by atmospheric cooling,
    (b) heating the irradiated target material in the heating zone in the presence of the oxidizing atmosphere at a temperature less than the melting point of said target material, said temperature being sufficient to drive off fission product gases, oxidize oxide-forming components of the target material and sublime sublimable materials including molybdenum-99 trioxide into said oxidizing atmosphere to form a gaseous mixture to be carried to said cooling zone, and
    (c) cooling the gaseous mixture in said cooling zone so that the sublimed materials including the molybdenum-99 trioxide are progressively condensed and collected at successive locations in the cooling zone in the form of substantially separate deposits.

* * * * *